United States Patent
Lorraine et al.

(10) Patent No.: US 10,588,541 B2
(45) Date of Patent: Mar. 17, 2020

(54) MAGNETIC TRACKER SYSTEM AND METHOD FOR USE FOR SURGICAL NAVIGATION

(71) Applicant: General Electric Company, Schenectady, NY (US)

(72) Inventors: Peter William Lorraine, Niskayuna, NY (US); Floribertus P. M. Heukensfeldt Jansen, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 410 days.

(21) Appl. No.: 14/332,015

(22) Filed: Jul. 15, 2014

(65) Prior Publication Data

US 2016/0015292 A1 Jan. 21, 2016

(51) Int. Cl.
*A61B 34/20* (2016.01)
*A61B 5/06* (2006.01)

(52) U.S. Cl.
CPC .............. *A61B 5/062* (2013.01); *A61B 34/20* (2016.02); *A61B 2034/2051* (2016.02); *A61B 2562/0223* (2013.01)

(58) Field of Classification Search
CPC ................................ A61B 5/062; A61B 34/20
See application file for complete search history.

(56) References Cited

U.S. PATENT DOCUMENTS

| | | | |
|---|---|---|---|
| 5,729,129 A * | 3/1998 | Acker | 324/207.12 |
| 6,104,185 A * | 8/2000 | Lamm | G01P 3/487 |
| | | | 324/207.12 |
| 6,980,921 B2 | 12/2005 | Anderson et al. | |
| 7,158,754 B2 | 1/2007 | Anderson | |
| 7,321,228 B2 * | 1/2008 | Govari | 324/207.17 |
| 7,573,258 B2 | 8/2009 | Anderson | |
| 7,782,046 B2 | 8/2010 | Anderson | |
| 7,902,817 B2 | 3/2011 | Anderson | |
| 7,957,925 B2 | 6/2011 | Nieminen et al. | |

(Continued)

FOREIGN PATENT DOCUMENTS

| | | |
|---|---|---|
| CN | 102651627 A | 8/2012 |
| WO | 2003000132 A1 | 1/2003 |

OTHER PUBLICATIONS

Lu W et al., "SEMAC: Slice Encoding for Metal Artifact Correction in MRI", Magn Reson Med., pp. 66-76, vol. 62 , Issue 1, Jul. 2009.

*Primary Examiner* — Mohamed Charioui
*Assistant Examiner* — Christine Y Liao (57) ABSTRACT

A method and system for magnetically tracking a device of interest generating a plurality of pre-determined multi-frequency signals. The method and system transmits a plurality of magnetic fields from a transmitter circuit based on the corresponding pre-determined multi-frequency signals. The magnetic fields propagating through an area of examination encompassing the device of interest and a magnetic sensor coupled to the device of interest. The method and system generate a sensor signal at the magnetic sensor indicative of field strength of the magnetic fields transmitted by the transmitter circuit. Further, the method and system determine a position of the magnetic sensor relative to the transmitter circuit based on the multi-frequency signals and the sensor signal.

18 Claims, 7 Drawing Sheets

(56) References Cited

U.S. PATENT DOCUMENTS

| | | |
|---|---|---|
| 8,249,689 B2 | 8/2012 | Anderson |
| 8,526,688 B2 | 9/2013 | Groszmann et al. |
| 2007/0265690 A1* | 11/2007 | Lichtenstein ............ A61B 5/06 607/116 |
| 2008/0001756 A1 | 1/2008 | Dimmer et al. |
| 2008/0036652 A1* | 2/2008 | Shore ....................... 342/357.06 |
| 2010/0113919 A1 | 5/2010 | Maschke |
| 2010/0127696 A1 | 5/2010 | Huber et al. |
| 2010/0137705 A1 | 6/2010 | Jensen et al. |
| 2010/0138183 A1 | 6/2010 | Jensen et al. |
| 2010/0151587 A1 | 6/2010 | Kojima et al. |
| 2010/0249571 A1 | 9/2010 | Jensen et al. |
| 2010/0305427 A1 | 12/2010 | Huber et al. |
| 2011/0224537 A1 | 9/2011 | Brunner |
| 2012/0165657 A1 | 6/2012 | Groszmann et al. |
| 2013/0166002 A1 | 6/2013 | Jung et al. |
| 2013/0184561 A1* | 7/2013 | Edelman ............... A61B 5/0263 600/413 |
| 2013/0270067 A1* | 10/2013 | Papsdorf ........... A61F 13/15764 198/377.01 |
| 2014/0005517 A1 | 1/2014 | Nagarkar et al. |
| 2014/0005527 A1 | 1/2014 | Nagarkar et al. |
| 2014/0187915 A1 | 7/2014 | Yaroshenko et al. |

\* cited by examiner

MAGNETIC TRACKER SYSTEM AND METHOD FOR USE FOR SURGICAL NAVIGATION

BACKGROUND

This disclosure relates generally to surgical navigation and more particularly to a magnetic tracker system and method for use for surgical navigation utilizing an excitation scheme using a plurality of frequencies.

Surgical navigation systems (SNS) frequently track the precise position and orientation of surgical instruments (e.g., catheters), implants or other medical devices, conventionally, in relation to multidimensional images of an anatomy of a patient using a tracker system. Additionally, SNS includes visualization tools to provide the surgeon with co-registered views of these surgical instruments, implants or other medical devices within the region of interest.

The multidimensional images may be generated either prior to or during the surgical procedure. For example, any suitable medical imaging technique, such as an X-ray, computed tomography (CT), magnetic resonance (MR), positron emission tomography (PET), ultrasound, or any other suitable imaging technique, as well as any combinations thereof may be utilized. After registering the multidimensional images to the position and orientation of the patient, or to the position and orientation of an anatomical feature or region of interest, the combination of the multidimensional images with graphical representations of the navigated surgical instruments, implants or other medical devices provides position and orientation information that allows a medical practitioner to manipulate the surgical instruments, implants or other medical devices to desired positions and orientations.

Conventional SNS include tracker systems that use position and orientation sensors, or sensing sub-systems based on, for example, electromagnetic (EM), radio frequency (RF), optical (line-of-sight), and/or mechanical technology.

EM sensors are typically implemented with coils or microcoils to generate and detect the magnetic fields. While coil based EM sensors have been successfully implemented, they may be susceptible to magnetic field distortions that arise from eddy currents in nearby conducting objects, such as, metal objects surrounding the patient. The tracking technique used with coil based EM sensors relies on a stable magnetic field, or a known magnetic field map. Therefore, unpredictable disturbances resulting from metallic objects in the magnetic field reduce the accuracy or may even render the tracking technique useless without additional position measurements, such as, from a medical image (e.g., CT, MR, PET). Therefore, there is a need for a tracker system to minimize or remove magnetic field distortions without reducing sensitivity of the EM sensors.

BRIEF DESCRIPTION

In an embodiment, a method for magnetically tracking a device of interest (e.g., a medical device) generating a plurality of pre-determined multi-frequency signals including multi-frequency per transmitter element. The method includes transmitting a plurality of magnetic fields from a transmitter circuit based on the corresponding pre-determined multi-frequency signals. The magnetic fields propagate through an area of examination encompassing the device of interest and a magnetic sensor coupled to the device of interest. The method includes generating a sensor signal at the magnetic sensor indicative of field strength of the magnetic fields transmitted by the transmitter circuit. Further, the method includes determining a position of the magnetic sensor relative to the transmitter circuit based on the multi-frequency signals and the sensor signal.

Optionally, the method may include identifying at least one of the magnetic fields from the transmitter circuit based on at least first and second frequencies of the multi-frequency signal. The position of the magnetic sensor may further be determined from the magnetic field identified.

Optionally, the sensor signal may include a secondary component caused by a secondary magnetic field created by passive sources within the area of examination such as a piece of conducting metal. Optionally, the method may include isolating at least one of the magnetic fields transmitted by the transmit circuit from the sensor signal based on at least first and second frequencies of the multi-frequency signal so as to isolate or eliminate the secondary field. The position of the magnetic sensor may further be determined from the magnetic field isolated.

In another embodiment, a magnetic tracking system for tracking a device of interest. The system includes a transmitter circuit configured to generate a plurality of magnetic fields based on corresponding pre-determined multi-frequency signals. The magnetic fields propagating through an area of examination. The system also includes a magnetic sensor coupled to the device of interest. The magnetic sensor is configured to generate a sensor signal indicative of field strength of the magnetic fields transmitted by the transmitter circuit when positioned within the area of examination. The system also includes a controller configured to determine a position of the magnetic sensor relative to the transmitter circuit based on the pre-determined multi-frequency signals and the sensor signal.

DETAILED DESCRIPTION

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide a magnetic tracker system or method of use to locate a device of interest. The system or method of use utilizes a plurality of predetermined multi-frequency signals to generate more than one magnetic field from a transmitter circuit. A magnetic sensor (MS) is placed, for example, at an end of surgical instruments (e.g., catheters), implants, or other medical devices to measure the magnetic field relative to its position within or approximate to a region of interest. The magnetic sensor outputs the magnetic field measurements to a controller. The controller determines the position of the MS relative to a reference sensor, the transmitter circuit, or within a medical image based on the multi-frequency signals and the magnetic field measurements. Optionally, the controller may filter or isolate distorted or secondary magnetic fields from the magnetic field measurements when determining the position of the MS.

Figure 1:
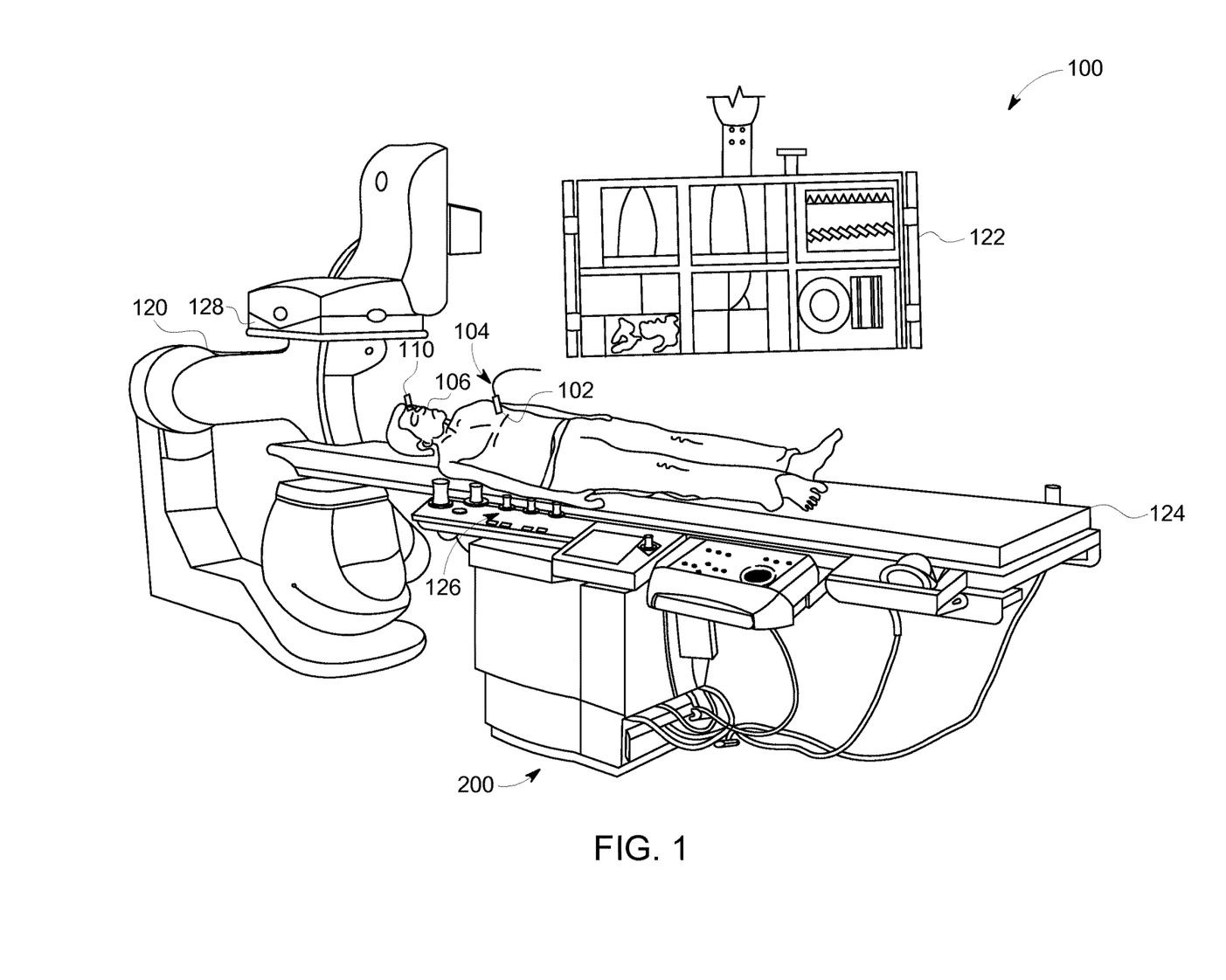
FIG. 1 is a schematic diagram of a surgical navigation system, in accordance with various embodiments.

FIG. 1 is a schematic diagram of a surgical navigation system (SNS) 100, of an embodiment, using magnetic tracking. A medical device 104 (e.g., surgical instrument, medical implant, catheter, guidewires, endovascular or gastrointestinal instruments) is placed within a region of interest of a patient 106. It should be noted that in other embodiments, a non-medical device 104 may be used such as user interface controllers (e.g., joysticks, pointers, keyboards), personnel locators, or any device of interest. A table 124 is positioned near the medical device 104 to support the patient 106 during the medical procedure. The medical device 104 is positioned near or within the patient 106. The medical device 104 includes a magnetic sensor (MS) 102 attached, for example, at the distal or proximal end of a medical device 104. The MS 102 measures a field strength or a field strength and direction of a magnetic field applied to the MS 102 where the magnetic field is generated from a transmitter circuit 126. The MS 102 may be, for example, a magnetoresistance sensor that exhibits a change in electrical resistance corresponding to the magnetic field to which the MS 102 is exposed, as disclosed in U.S. Pat. No. 8,358,128, entitled "SURGICAL NAVIGATION SYSTEM WITH MAGNETORESISTANCE SENSORS", which is expressly incorporated herein by reference. Additionally or alternatively, the MS 102 may be a coil, tri-coil, Hall Effect sensor, flux gate device, or any suitable device, which is capable of generating a signal indicative of the a field strength or a field strength and direction of the magnetic field.

Figure 2:
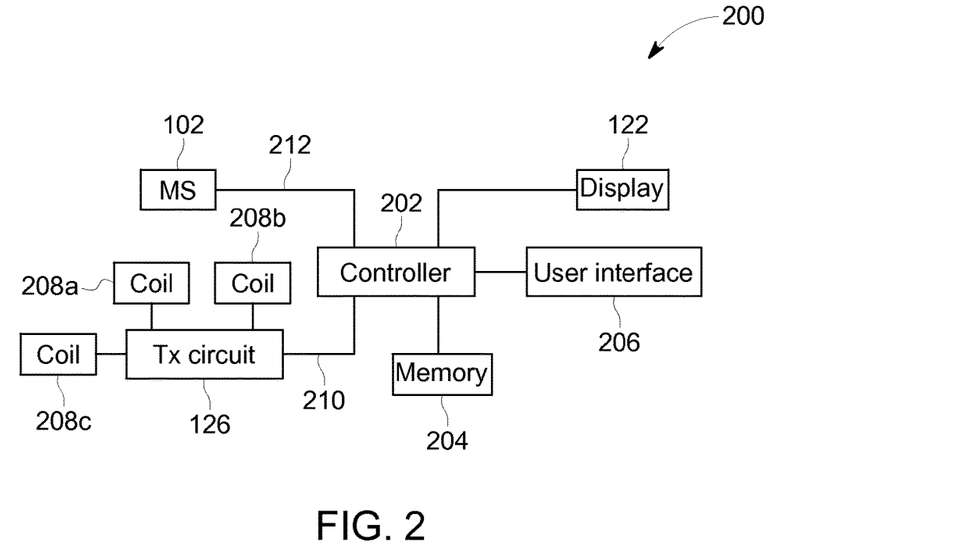
FIG. 2 is a schematic block diagram of a magnetic tracker system, in accordance with various embodiments.

A magnetic tracker system (MTS) 200, shown in FIG. 2, is provided to determine a position (e.g., Cartesian coordinate, polar coordinate, cylindrical coordinate) and/or orientation (e.g., pitch, roll, yaw) of the medical device 104 within the body or region of interest of the patient 106. The MTS 200 may comprise, for example, the systems generally shown and described in, U.S. Pat. Nos. 7,902,817, 7,911,202, and 7,782,046 all of which are expressly incorporated by reference in their entirety. Optionally, the position and/or orientation may be determined in relation to one or more reference sensors, for example, a patient reference sensor 110 which may be maintained stationary during the procedure. Additionally or alternatively, the position and/or orientation may be determined in relation to one or more alternative MS and/or medical devices 104. The MTS 200 includes the transmitter circuit 126, which generates magnetic fields within the region of interest. The MS 102 associated with the medical device 104, generates an output that is responsive to the magnetic field based on a relative position (e.g., distance from the transmitter circuit 126) of the MS 102 within the magnetic field. The MS 102 transmits (e.g., wire conductor, wirelessly) the output to a controller 202 of the MTS 200, which is used to determine a position of the MS 102.

The transmitter circuit 126 may include a plurality of coils 208a-c arranged, for example, orthogonally to one another to produce a magnetic field in and/or proximate to the region of interest of the patient 106. For example, the coils 208a-c may each be a magnetic dipole (e.g., coils, current loops, electromagnets, electromagnetic coil) capable of producing a dipole magnetic field when a current is applied. When a current is provided across a magnetic dipole, a single magnetic field may be generated with a magnitude moment vector along its "axis." For each coil 208a-c the direction of the coil axis is perpendicular to the plane of the coil in accordance with the right-hand rule. Those of ordinary skill in the art will appreciate that multiple transmitting coils may be used in coordination to generate multiple magnetic fields. Each of the coils may propagate magnetic fields along a plane that corresponds to a coordinate system (e.g., Cartesian coordinate (X, Y, Z)) of the magnetic tracker system 200. For example, the coil 208a may propagate a magnetic field along an X plane, the coil 208b may propagate a magnetic field along a Y plane, and the coil 208c may propagate a magnetic field along a Z plane. It should be noted, that the transmitter circuit 126 may include more than or less than three coils (e.g., 12 coils, 1 coil). Further, the coils 208a-c may be in alternative arrangements as generally described in U.S. Pat. Nos. 7,158,754, 7,573,258 and 7,902,817, all of which are expressly incorporated by reference in their entirety. Although the transmitter circuit 126 is shown positioned under the patient 106 and the table 124 in FIG. 1, the transmitter circuit 126 may be placed in another location, for example, attached to a radiation emitter 128 of an imaging system 120.

The controller 202 of the MTS 200 may include or represent hardware circuits or circuitry that include and/or are connected with one or more logic based devices, such as processors, microprocessors, microcontrollers, or other logic based devices (and/or associated hardware, circuitry, and/or software stored on a tangible and non-transitory computer readable medium or memory). The controller 202 may receive a plurality of input signals including signals generated by the MS 102, the medical device 104, a user interface 206 (e.g., keyboard, touchscreen, buttons, or the like), and one or more patient reference sensors 110 and generate a plurality of output signals including those used to control the medical device 104 and/or a display 122. The controller 202 may also receive an input signal from an organ monitor (e.g., ECG monitor, respiratory sensor, or the like).

Optionally, the SNS 100 may include an imaging system 120. The imaging system 120 may be provided to acquire images of the region of interest (e.g., an organ). The imaging system 120 may, for example, comprise of a fluoroscopic imaging system, computed tomography (CT) imaging systems, a three-dimensional radio angiography (3DRA) system, magnetic resonance (MR), positron emission tomography (PET), single-photon emission computed tomography (SPECT), X-ray, or the like. The controller 202 may correlate or register the positional data determined from the MS 102 with, or based on, one or more medical images acquired from the imaging system 120, as generally describe and shown in U.S. Pat. No. 8,526,688, entitled "METHODS AND SYSTEMS FOR REGISTRATION OF SURGICAL NAVIGATION DATA AND IMAGE DATA", which is expressly incorporated herein by reference.

Figure 3:
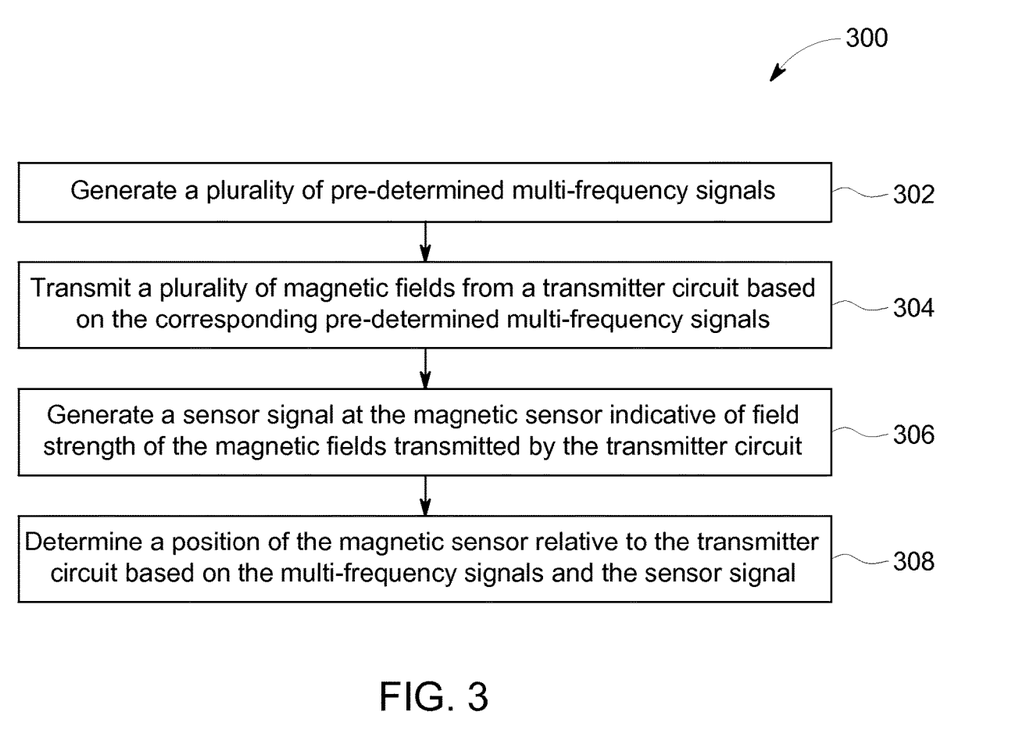
FIG. 3 is a flowchart of a method for magnetic tracking, in accordance with various embodiments.

FIG. 3 illustrates a flowchart of a method 300 for magnetic tracking for surgical navigation. The method 300, for example, may employ structures or aspects of various embodiments (e.g., systems and/or methods) discussed herein (e.g., the SNS 100 in FIG. 1, the MTS in FIG. 2). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of a magnetic tracker for surgical navigation. It should be noted, other methods may be used, in accordance with embodiments herein.

At least one technical effect of at least one portion of the methods described herein is at least (i) generate a plurality of pre-determined multi-frequency signals, (ii) transmit a plurality of magnetic fields from a transmitter circuit based on the corresponding pre-determined multi-frequency signals, (iii) generate a sensor signal at the magnetic sensor indicative of a field strength of the magnetic fields transmitted by the transmitter circuit, and (iv) determine a position of the magnetic sensor based on the multi-frequency signals and the sensor signal.

Figure 4:
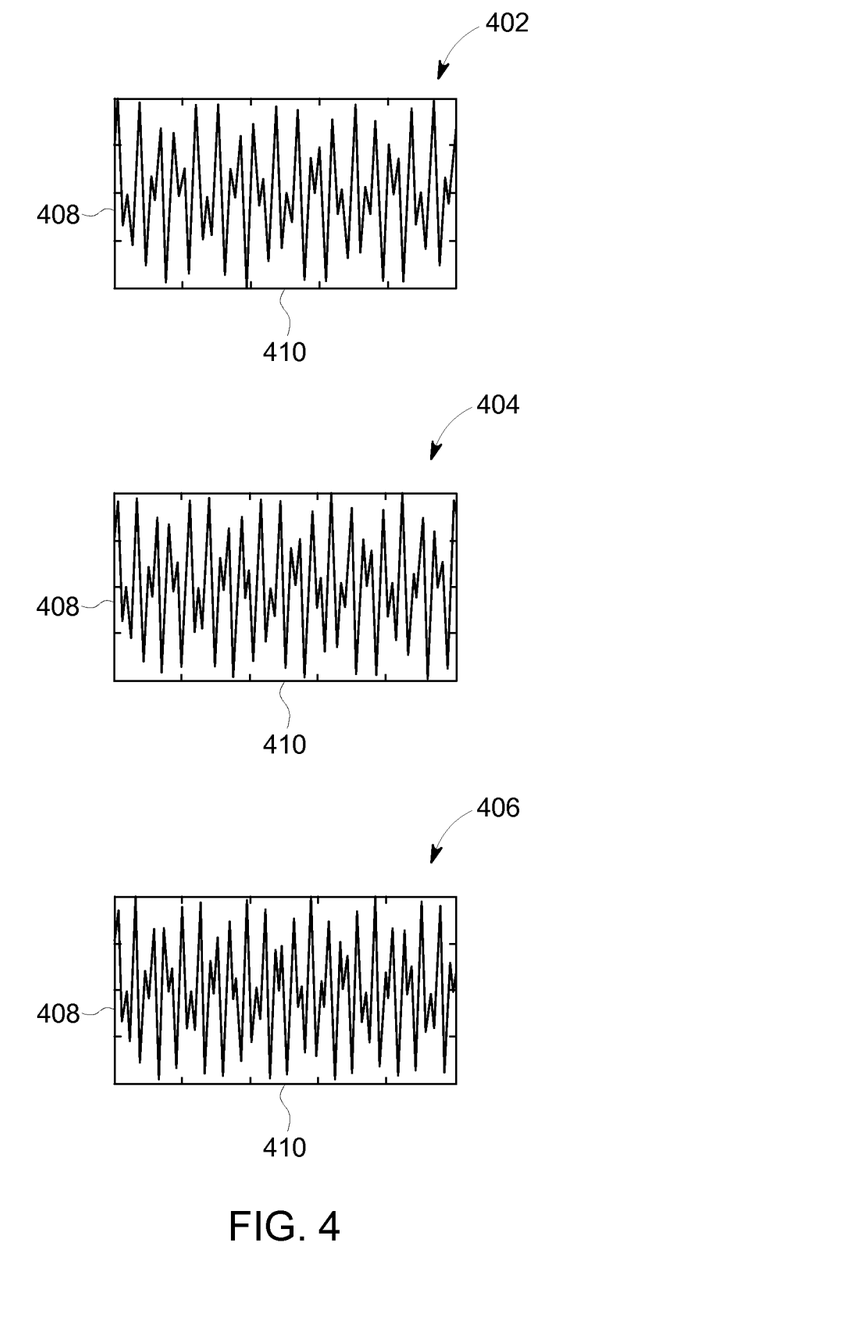
FIG. 4 is an illustration of thee multi-frequency signals generated by a controller in accordance with various embodiments.

Beginning at 302, the method 300 generates a plurality of pre-determined multi-frequency signals. FIG. 4 illustrates three graphical representations of three different pre-determined multi-frequency signals 402-404 generated by the controller 202 in accordance with an embodiment herein. The vertical axis 408 represents a current amplitude and the horizontal axis 410 represents time. The pre-determined multi-frequency signals 402-406 may each represent a sum of multiple sinusoidal signals from a set of pre-determined frequencies. It should be noted that greater or less than three multi-frequency signals 402-404 may be generated in other embodiments. Optionally, the pre-determined multi-frequency signals 402-406 may be based on a frequency modulation scheme or a multi-tone multi frequency signaling.

For example, the multi-frequency signal 402 may represent the sum of two sinusoidal signals having predetermined frequencies of 139.4 Hz and 241.8 Hz, respectively. The predetermined frequencies may be incoherent or orthogonal with respect to each other such that the predetermined frequencies do not have a harmonic relationship with one another. For example, the multi-frequency signal 404 may represent the sum of a sinusoidal signals having predetermined frequencies of 154 Hz and a 267.2 Hz, respectively, and the multi-frequency signal 406 may represent the sum of sinusoidal signals having predetermined frequencies of 170.4 Hz and 295.4 Hz. It should be noted that the predetermined frequencies may be higher or lower than used in the above example, and the signals may not be sinusoidal. The predetermined frequencies may be in a range between 100-300 Hz. Additionally or alternatively, the predetermined frequencies may be in a range between 10-22 kHz.

Figure 5:
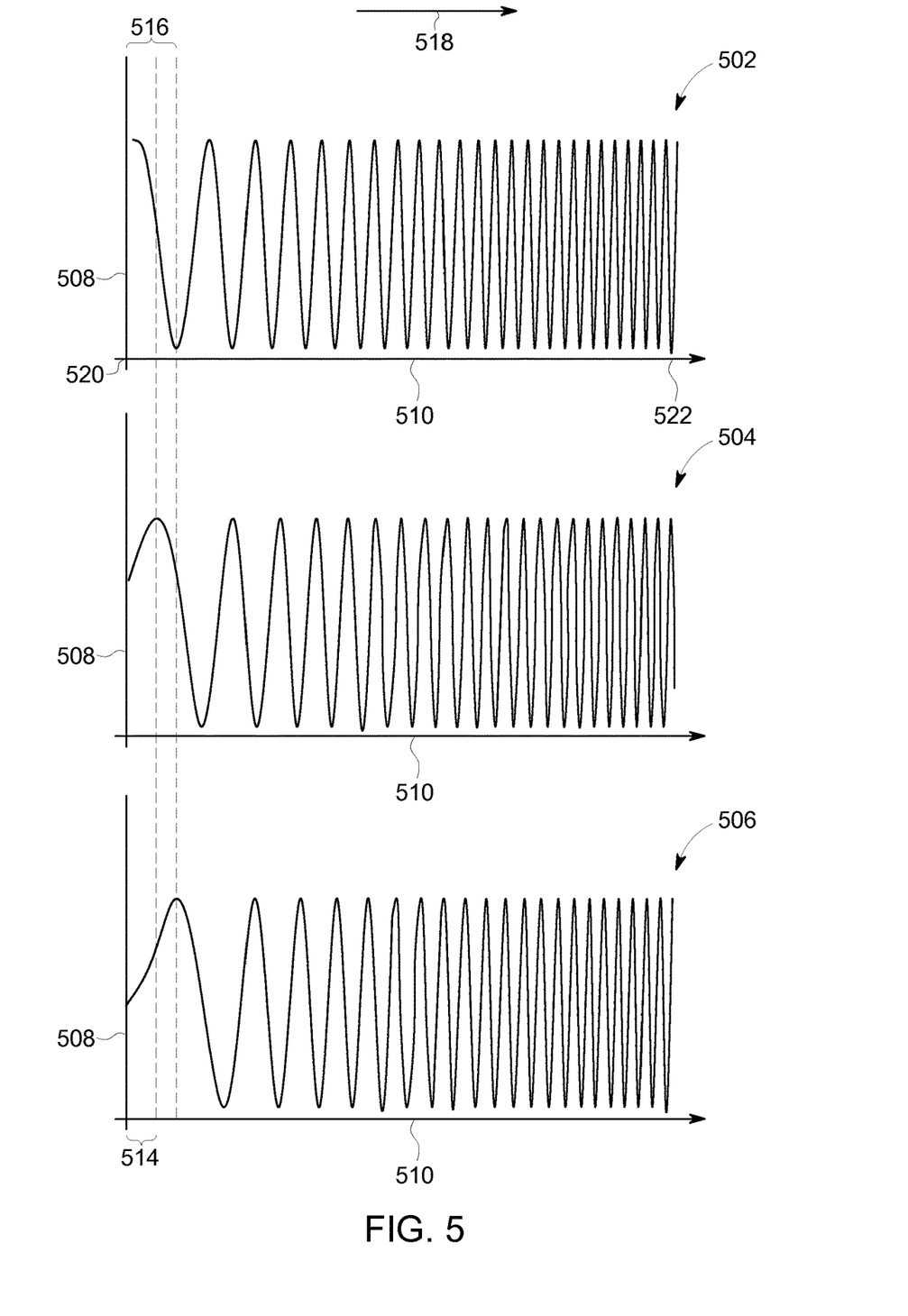
FIG. 5 is an illustration of three multi-frequency signals generated by a controller in accordance with various embodiments.

Additionally or alternatively, the pre-determined multi-frequency signals may represent a series of signals in which the instantaneous frequency increases or decreases over time, for example, a chirp signal. FIG. 5 illustrates a graphical representation of different pre-determined multi-frequency signals 502-506 with changing instantaneous frequencies that are generated by the controller 202 in accordance with an embodiment herein. The vertical axis 508 represents a current amplitude and the horizontal axis 510 represents time. The frequency of each multi-frequency signal 502-506 increases linearly over time in the direction of an arrow 518 at a predetermined rate. The multi-frequency signals 502-506 are phase shifted relative to each other such that each multi-frequency signal 502-506 has a different frequency and/or amplitude at an instantaneous point in time. For example, the multi-frequency signal 504 has a phase shift 514 relative to the multi-frequency signal 502, and the multi-frequency signal 506 has a phase shift 516 relative to the multi-frequency signal 502.

Figure 6:
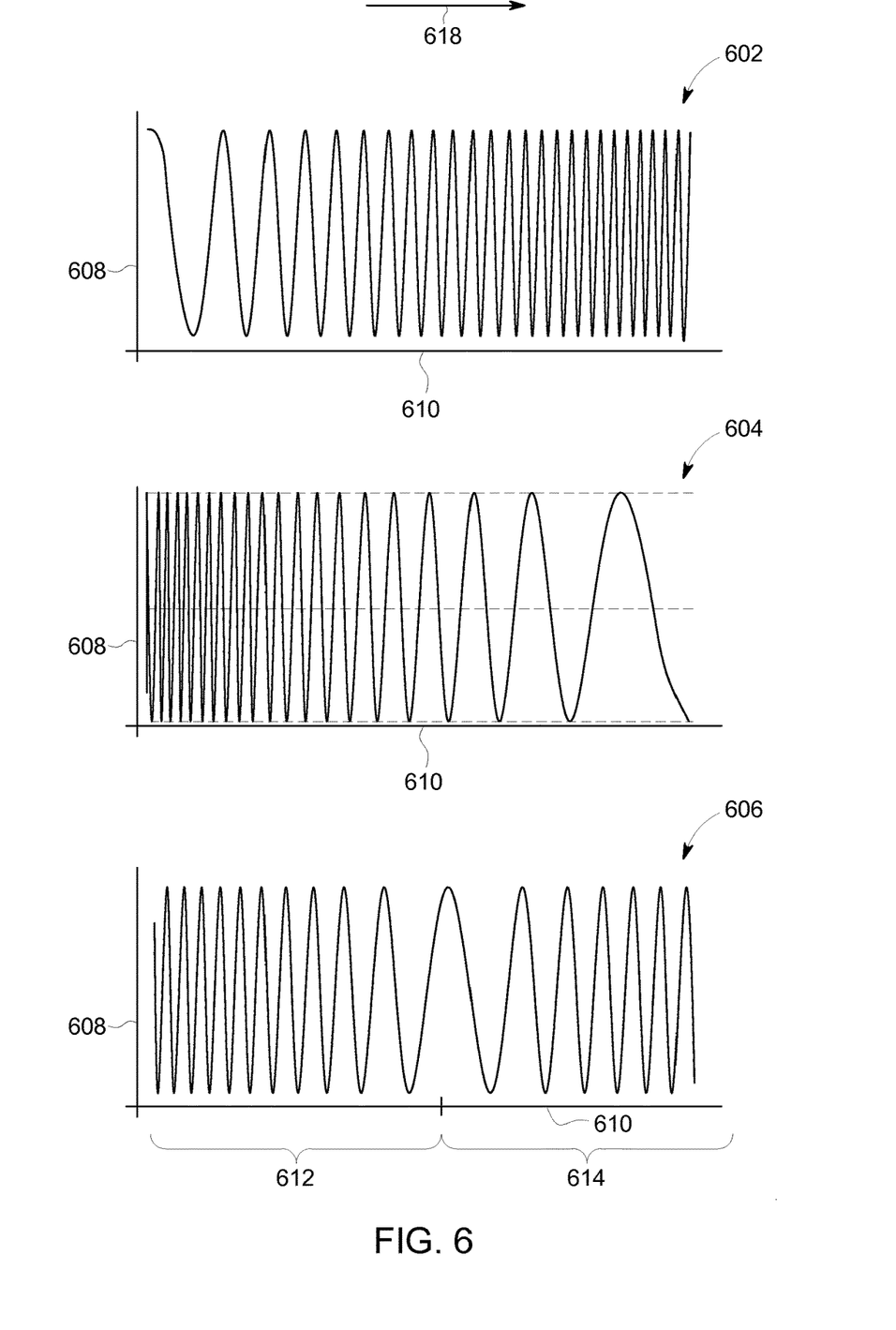
FIG. 6 is an illustration of three multi-frequency signals generated by a controller in accordance with various embodiments.

It should be noted in other embodiments, the frequency of the multi-frequency signal 502-506 may decrease linearly, increase/decrease exponentially over time, and/or the rate of frequency changes may be different or asymmetric relative to each multi-frequency signal 502-506. FIG. 6 illustrates three graphical representations of three different pre-determined multi-frequency signals 602-606 generated by the controller 202 in accordance with an embodiment herein. The vertical axis 608 represents a current amplitude and the horizontal axis 610 represents time. The frequency of the multi-frequency signal 602 increases linearly over time in the direction of an arrow 618 at a predetermined rate. The frequency of the multi-frequency signal 604 decreases exponentially over time in the direction of the arrow 610. The frequency of the multi-frequency signal 606 increases for a set period 612 and decreases for a period 614.

It should be noted that the graphical representations of the pre-determined multi-frequency signals 502-506 and 602-606 illustrated in FIGS. 5-6 may be a portion of a continuous signal repeating the illustrated portion segment. Additionally or alternatively, the multi-frequency signals 502-506 and 602-606 may be repeated after reaching a set frequency threshold. For example, the multi-frequency signal 502 may increase linearly at a predetermined rate from 100 Hz at 520, once the multi-frequency signal 502 reaches a threshold of 300 Hz at 522 the multi-frequency signal 502 may return to a frequency of 100 Hz. Optionally, the multi-frequency signal 502 may decrease at the predetermined rate until the frequency of 100 Hz is reached, set as a minimum threshold, and the frequency of the multi-frequency signal 502 is increased again at the predetermined rate.

Optionally, the pre-determined multi-frequency signal may be based on a frequency-shift key or a multi-frequency shift key.

Optionally, the pre-determined multi-frequency signals may be a non-sinusoidal waveform such as a square wave or binary code/sequence. For example, each of the multi-frequency signals may be a separate pseudo-random sequence of bits or binary Golay code. The controller 202 may include a filtering or post-acquisition algorithm to identify or separate the pre-determined multi-frequency signals for each coil 208a-c. Additionally or alternatively, the controller 202 or a clinician using the user interface 206 may adjust or select pre-determined multi-frequency signals based on a desired signal to noise ratio.

Returning to FIG. 3, at 304, a plurality of magnetic fields are transmitted from the transmitter circuit 126 based on the corresponding pre-determined multi-frequency signals (e.g., 402-406). The transmitter circuit 126 may energize the plurality of coils 206a-c using corresponding multi-frequency signals (e.g., 402-406) to generate magnetic fields. For example, the transmitter circuit 126 may receive the predetermined multi-frequency signals from the controller 202 through a communication bus 210. The transmitter circuit 126 may include drive circuitry to provide a drive current, such as the multi-frequency signal, to energize each of the coils 206a-c. For example, the transmitter circuit 126 may output drive currents corresponding to the multi-frequency signal 402, 404, and 406 to the coil 206a, 206b, and 206c, respectively. Optionally, the transmitter circuit 126 may be integrated with the controller 202. Additionally or alternatively, the transmitter circuit 126 may generate the multi-frequency signals based on instructions from the controller 202 through the communication bus 210.

The magnetic fields propagate outward from the transmitter circuit 126 through an area of examination where the patient 106, device of interest (e.g., medical device 104), and MS 102 are located. As the magnetic fields propagate about the MS 102, the MS 102 generate a sensor signal indicative of a field strength or field strength and direction of the magnetic field to which the MS 102 is exposed.

Figure 7:
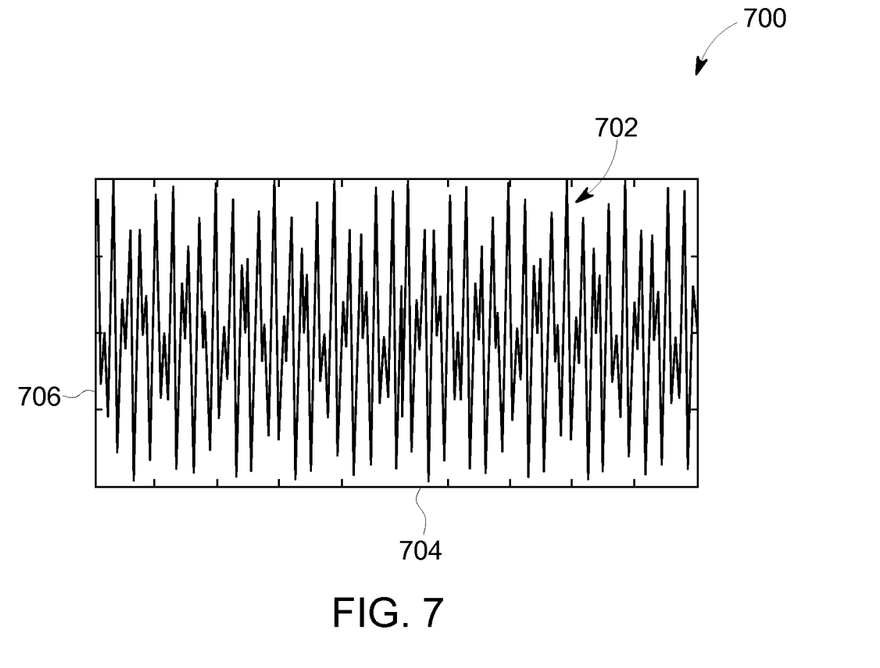
FIG. 7 is a graphical illustration of measurements received from a magnetic sensor, in accordance with various embodiments.

At 306, the MS 102 generates a sensor signal indicative of a field strength of the magnetic fields transmitted by the transmitter circuit 126. The MS 102 delivers the sensor signal to the controller 202. FIG. 7 is a graphical representation 700 of the sensor signal as a measurement curve 702 from the MS 102, over time, received by the controller 202. The horizontal axis 704 represents time and the vertical axis 706 represents a field strength or magnitude (e.g., magnetic flux density) of a magnetic field measured by the MS 102 at its current position, for example, in units of tesla. The controller 202 may receive the sensor signal represented by the measurement curve 702 via a communication bus 212. Optionally, the controller 202 may receive the measurements wirelessly using wireless communication interfaces and protocols (e.g., Bluetooth low energy, medical implant communication service, ZigBee, WiFi).

At 308, the controller 202 determines a position of the MS 102 relative to the transmitter circuit 126 based on the multi-frequency signals and the sensor signal. The controller 202 may isolate the field strength of the measured magnetic field corresponding to a direction or plane based on the magnetic fields generated by the coils 208a-c that are driven by the pre-determine multi-frequency signals. For example, the coil 208a may be driven by a multi-frequency signal with frequencies at 820 and 826, the coil 208b may be driven by a multi-frequency signal with frequencies at 810 and 816, and the coil 208c may be driven by a multi-frequency signal with frequencies at 82 and 818. The controller 202 may calculate a Fourier Transform (FT) of the measurement curve 702 from the time domain to a frequency domain to determine the field strength of the magnetic field at the frequencies of the multi-frequency signal.

Figure 8:
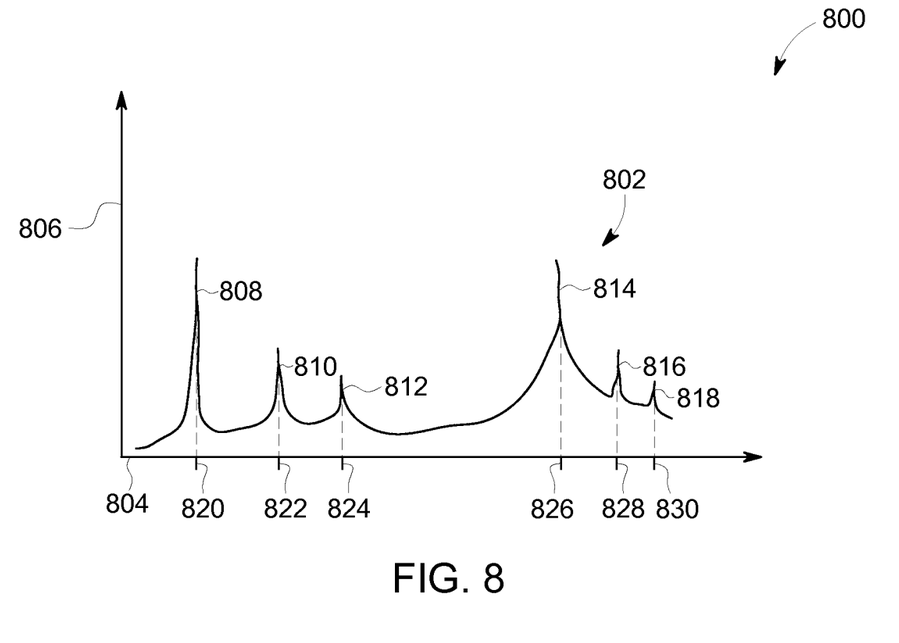
FIG. 8 is a graphical illustration of measurements received from a magnetic sensor, in accordance with various embodiments.

FIG. 8 is graphical representation 800 of a measurement curve 802 representing a Fourier Transform (FT) of the measurement curve 702 from FIG. 7. The horizontal axis 804 represents frequency and the vertical axis 806 represents a field strength of the measured magnetic field. The measurement curve 802 has six peaks 808-818 at the frequencies 820-830 that correspond to the magnetic fields generated by the multi-frequency signals of the coils 208a-c. The controller 202 may determine a position of the MS 102 based on the measured field strength of the magnetic fields that correspond to distance from the coils 208a-c as disclosed in U.S. Pat. Nos. 6,980,921 and 8,249,689, both of which are expressly incorporated by reference in their entirety. Optionally, the controller 202 may determine a coordinate (e.g., Cartesian coordinate, polar coordinate, cylindrical coordinate) of the MS 102 based on a coordinate system with an origin, for example, defined be the patient reference sensor 110.

Additionally or alternatively, the controller 202 may determine the position of the MS 102 using a phase dependent detection algorithm based on the phase of the pre-determined multi-frequency signals. For example, each of the coils 208a-c may be driven by the pre-determined multi-frequency signals 502-506, respectively. The phase dependent detection algorithm may isolate the magnetic fields generated by the coils 208a-c based on the phase shift 514-516 of the pre-determined multi-frequency signals 502-506.

It should be noted that the sensor signal may include measurements of magnetic fields not directly generated by the transmitter circuit 126, such as a secondary magnetic field or noise magnetic field, which affects the position calculations of the controller 202. The secondary field may be a distorting field from induced currents in a passive source. Optionally, a correction algorithm may be used by the controller 202 to identify and/or isolate only the reference magnetic fields (e.g., transmitter based magnetic fields) generated by the transmitter circuit 126. The secondary magnetic field may originate from non-ferromagnetic conducting structures, for example, instruments and/or gantries (e.g., the imaging system 120) proximate to the transmitter circuit 126 or within the area of examination. The secondary magnetic field may be caused by eddy currents induced within the non-ferromagnetic conducting structure in response to the generated magnetic fields from the transmitter circuit 112.

Figure 9:
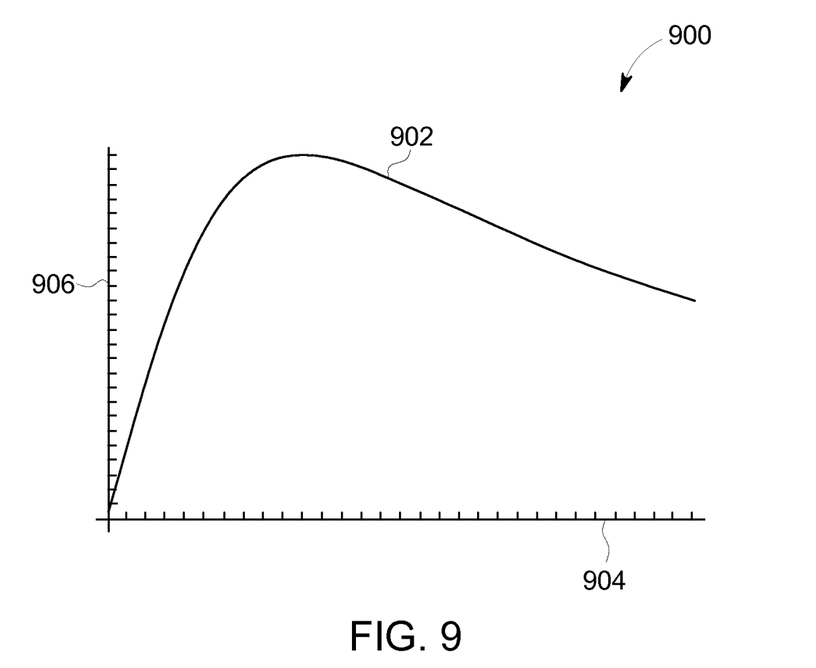
FIG. 9 is a graphical illustration of a measured magnetic field measurement in-phase with a transmitter field, in accordance with various embodiments.
Figure 10:
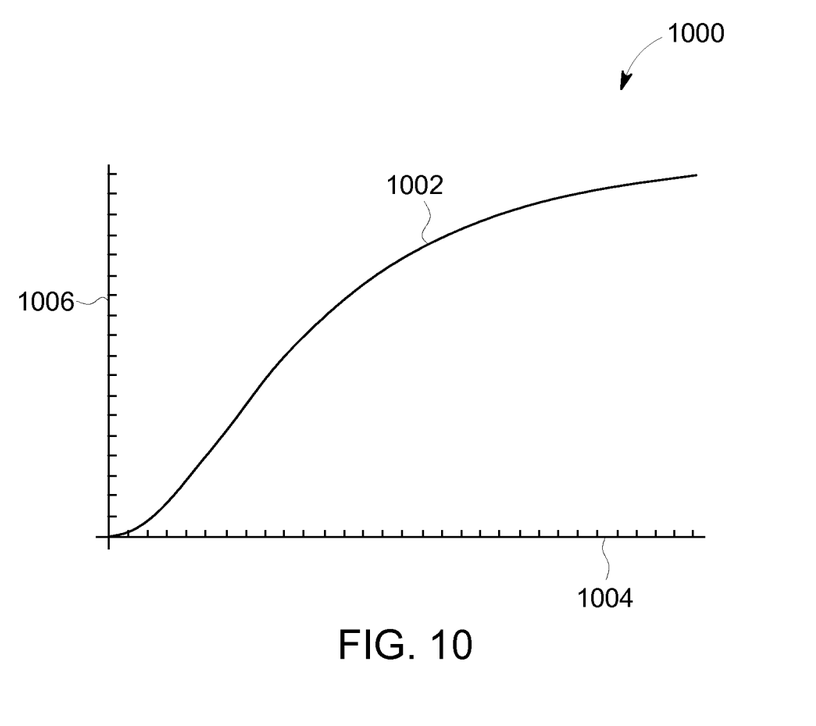
FIG. 10 is a graphical illustration of a measured magnetic field measurement out-of-phase with a transmitter field, in accordance with various embodiments.

FIGS. 9 and 10 are graphical illustrations of two curves 902 and 1002 based on the sensor signal generated by the MS 102 in the frequency domain. The vertical axes 906 and 1006 represent field strength (e.g., flux) and the horizontal axes 904 and 1004 represent frequency (ω). The curve 902 represents the magnetic field ($B_{real}$) measured by the MS 102 that is in phase with respect to the pre-determined multi-frequency signal used to generate the reference magnetic field of one of the coils 208a-c of the transmitter circuit 126. The curve 1002 represents the magnetic field ($B_{imaginary}$) measured by the MS 102 that is out of phase (e.g., 90° out of phase) with respect to the pre-determined multi-frequency signal.

The correction algorithm may utilize the equations 1 and 2 below to determine or identify the reference magnetic field from at least one of the coils 208a-c from the sensor signal, which may be used to determine the position of the MS 102. Additionally or alternatively, the correction algorithm may determine or identify the secondary magnetic field to remove or partition the secondary magnetic field from the sensor signal.

$$B_{real} = B_0 + B_{secondary} \cdot \frac{\omega}{R + L \cdot \omega^2} \quad \text{Equation (1)}$$

$$B_{imaginary} = B_{secondary} \cdot \frac{L \cdot \omega^2}{R^2 + L^2 \cdot \omega^2} \quad \text{Equation (2)}$$

It should be noted that the secondary magnetic field, represented as the variable $B_{induced}$, is included in both the in ($B_{real}$) and out ($B_{imaginary}$) of phase magnetic field measured by the MS 102. The reference magnetic field by one of the coils 208a-c, represented as the variable $B_0$, is included in the in phase magnetic field ($B_{real}$). The variables R and L, represent the resistance and inductance, respectively, of the non-ferromagnetic conducting structures that generate the secondary magnetic field ($B_{secondary}$). It should be noted that in other embodiments, other equations may be used that describe the distorting field.

The controller 202, using the correction algorithm, calculates the reference magnetic field ($B_0$) by measuring the magnetic fields (both in and out of phase) from at least two frequencies. For example, the controller 202 may determine the reference magnetic field ($B_0$) for the coil 208a. The coil 208a is driven by the multi-frequency signal having frequencies at 820 and 826 from FIG. 8. The two frequencies result in a $B_{real}$ and $B_{imaginary}$ corresponding to the frequency (ω) at 820, and a $B_{real}$ and $B_{imaginary}$ corresponding to the frequency (ω) at 826. Based on the four measured magnetic field measurements, the controller 202 may determine the reference magnetic field ($B_0$) generated by the coil 208a as well as the remaining variables $B_{induced}$, R, and L using equations 1 and 2. The controller 202 may repeat the correction algorithm to determine the reference magnetic field for the remaining coils 208b-c of the transmitter circuit 126. The controller 202 may determine a position of the MS 102 based on the reference magnetic fields for each coil 208a-c determined using the correction algorithm.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for magnetically tracking a device of interest, the method comprising:
    generating a plurality of pre-determined multi-frequency signals, wherein the pre-determined multi-frequency signals are phase shifted with respect to each other;
    transmitting a plurality of magnetic fields from a transmitter circuit based on the corresponding pre-determined multi-frequency signals, the magnetic fields propagating through an area of examination encompassing the device of interest and a magnetic sensor coupled to the device of interest;
    generating a sensor signal at the magnetic sensor indicative of a field strength of the magnetic fields transmitted by the transmitter circuit;
    determining a direction of the magnetic fields with respect to the magnetic sensor based on the phase shift between the pre-determined multi-frequency signals;
    determining a position of the magnetic sensor relative to the transmitter circuit based on the multi-frequency signals and the sensor signal;
    determining at least one of: a position and an orientation of the device of interest in relation to the determined position of the magnetic sensor; and
    manipulating the device of interest to at least one of: a desired position and a desired orientation.

2. The method of claim 1, further comprising identifying at least one of the magnetic fields from the transmitter circuit based on at least first and second frequencies of the multi-frequency signals; and
    wherein the position of the magnetic sensor is determined from the at least one of the magnetic fields that is identified.

3. The method of claim 1, wherein the multi-frequency signals are at least one from a group comprising a chirp signal, a frequency modulated signal, pseudo-random bit sequence, frequency shift keying, multiple frequency shift keying, multi-tone multi frequency signaling, or a Golay code.

4. The method of claim 1, wherein the sensor signal includes a secondary component induced by a secondary magnetic field created by passive sources within the area of examination, the method further comprising excluding the second component from calculations of the position based on the multi-frequency signals.

5. The method of claim 4, further comprising isolating at least one of the magnetic fields transmitted by the transmit circuit from the sensor signal based on at least first and second frequencies of the multi-frequency signal and electrical characteristics of the passive sources; and
    wherein the position of the magnetic sensor is determined from the at least one magnetic fields that is isolated.

6. The method of claim 1, wherein the magnetic sensor is a magneto-resistive sensor.

7. The method of claim 1, further comprising receiving a field strength measurement of the magnetic field from a second magnetic sensor.

8. The method of claim 7, wherein the position of the magnetic sensor is determined using known relative positions of the first and second magnetic sensors.

9. The method of claim 1, wherein the transmitter circuit is coupled to at least three electromagnetic coils.

10. The method of claim 1, further comprising registering the position of the magnetic sensor with at least one medical image to form a position registered medical image.

11. A magnetic tracking system for tracking a device of interest, the system comprising:
    a transmitter circuit configured to generate a plurality of magnetic fields based on corresponding pre-determined multi-frequency signals, wherein the pre-determined multi-frequency signals are phase shifted with respect to each other, the magnetic fields propagating through an area of examination;
    a magnetic sensor coupled to the device of interest, the magnetic sensor configured to generate a sensor signal indicative of a field strength of the magnetic fields transmitted by the transmitter circuit when positioned within the area of examination;

a controller configured to determine a position of the magnetic sensor relative to the transmitter circuit based on the pre-determined multi-frequency signals and the sensor signal, wherein the controller is further configured to determine a direction of the magnetic fields with respect to the magnetic sensor based on the phase shift between the plurality of pre-determined multi-frequency signals; and further wherein the controller is configured to determine at least one of: a position and an orientation of the device of interest in relation to the determined position of the magnetic sensor and manipulate the device of interest to at least one of; a desired position and a desired orientation.

12. The magnetic tracking system of claim 11, wherein the controller is further configured to identify at least one of the magnetic fields from the transmitter circuit based on at least first and second frequencies of the multi-frequency signals.

13. The magnetic tracking system of claim 11, wherein the multi-frequency signals are at least one from a group comprising of a chirp signal, a frequency modulated signal, pseudo-random bit sequence, frequency shift keying, multiple frequency shift keying, multi-tone multi-frequency signaling, or a Golay code.

14. The magnetic tracking system, of claim 11, wherein the sensor signal includes a secondary component induced by a secondary magnetic field created by passive sources within the area of examination, the controller is further configured to exclude the second component from calculations of the position based on the multi-frequency signals.

15. The magnetic tracking system of claim 14, wherein the controller is further configured to isolate at least one of the magnetic fields transmitted by the transmit circuit from the sensor signal based on at least first and second frequencies of the multi-frequency signals and electrical characteristics of the passive sources.

16. The magnetic tracking system of claim 11, wherein the magnetic sensor is a magneto-resistive sensor.

17. The magnetic tracking system of claim 11, further comprising a second magnetic sensor, wherein the controller is further configured to determine the position of the magnetic sensor relative to the second magnetic sensor.

18. The magnetic tracking system of claim 11, wherein the transmitter circuit is coupled to at least three electromagnetic coils.

* * * * *